United States Patent [19]

Glass et al.

[11] Patent Number: 5,208,362
[45] Date of Patent: May 4, 1993

[54] PROCESS FOR STABILIZING ORGANOPHOSPHORUS COMPOUNDS

[75] Inventors: Richard D. Glass; Vincent J. Gatto, both of Baton Rouge, La.

[73] Assignee: Ethyl Corporation, Richmond, Va.

[21] Appl. No.: 842,653

[22] Filed: Feb. 27, 1992

[51] Int. Cl.$^5$ .......................... C07F 9/40; C07F 9/20; C07F 9/18; C07F 9/142

[52] U.S. Cl. .................................... 558/146; 558/148; 558/150

[58] Field of Search ...................... 558/146, 148, 150

[56] References Cited

U.S. PATENT DOCUMENTS 4,402,858 9/1983 Capolupo et al. ............... 252/400.24
4,962,144 10/1990 Babillis et al. ...................... 524/118

FOREIGN PATENT DOCUMENTS 0400454 12/1990 European Pat. Off. .

OTHER PUBLICATIONS

*IUPAC Nomenclature of Organic Chemistry;* 1979 edition; Pergamon: New York, 1979; p. 395.

*Primary Examiner*—Mary C. Lee
*Assistant Examiner*—Michael G. Ambrose
*Attorney, Agent, or Firm*—Patricia J. Hogan

[57] ABSTRACT

Organophosphorus compounds are stabilized against decomposition during and after recovery from their synthesis reaction mixtures by the addition to the synthesis reaction mixture of at least 0.5% by weight of an acid scavenger, based on the weight of the organophosphorus compound, before allowing the organophosphorus compound to crystallize. The invention is of particular value in the stabilization of 2,2'-alkylidenebis(dialkylphenyl)fluorophosphonites, such as 2,2'-ethylidenebis(4,6-di-t-butylphenyl)fluorophosphite, which is rendered more suitable for use as a stabilizer for organic polymers, e.g., polycarbonates, by the practice of the invention.

19 Claims, No Drawings

PROCESS FOR STABILIZING ORGANOPHOSPHORUS COMPOUNDS

FIELD OF INVENTION

This invention relates to a process for stabilizing organophosphorus compounds, and more particularly to a process for stabilizing such compounds against acidic decomposition.

BACKGROUND

As disclosed in A. N. Pudovik, *Chemistry of Organophosphorus Compounds*, MIR Publishers (Moscow), 1989, pp. 68-92, it is known that organophosphorus compounds, such as phosphites and phosphonites, have a tendency to hydrolyze when exposed to moisture, that they can also be decomposed by a transesterification reaction when crystallized from alcohols, that these decomposition reactions are catalyzed by acids, but that the removal of trace amounts of acid impurities from the organophosphorus compounds is very time consuming and expensive.

U.S. Pat. No. 4,402,858 (Capolupo et al.) teaches that the hydrolysis of neat phosphites, i.e., phosphites already recovered from their synthesis reaction mixtures, can be minimized by blending them with certain metal carboxylates so as to provide phosphorus/metal atomic ratios of 78-900/1 in the blends. European Patent Application 0 400 454 (Enlow et al.) teaches that hydrolytic stability can be imparted to neat organophosphites by blending them with 50-200%, based on the weight of the organophosphite, of a metal soap, a metal oxide, or an alkali metal salt of an inorganic acid and optionally also with an inert support.

Although there is considerable value to minimizing decomposition of an organophosphorus compound after it has been prepared, e.g., during storage or during utilization in an end-use application, such as the stabilization of polymers and other materials, it has been found that decomposition—sometimes extensive decomposition—can occur even before the organophosphorus compound is recovered from its synthesis reaction mixture, even under anhydrous or substantially anhydrous conditions, but especially when alcoholic solvents are used in the crystallization.

It is advantageous, i.e., both simple and inexpensive, to recover organophosphorus compounds by crystallization from alcohols. However, the nature of alcohols is such that they promote decomposition of the organophosphorus compounds both by reacting with the compounds themselves and by containing water which can also react with the compounds. These reactions lead to lower product yields and increase the formation of impurities.

The acid-catalyzed decomposition of organophosphorus compounds during recovery from its synthesis reaction mixture is a problem, not only because of its reducing the yield of the desired product, but because the impurities contributed by the decomposition can prevent the organophosphorus compound product from being usefully employed in some applications. However, as already indicated, removal of the trace amounts of acid impurities that catalyze the decomposition is too time consuming and expensive to be a satisfactory solution to the problem, especially when the organophosphorus compounds are prepared on a production scale.

SUMMARY OF INVENTION

It has now been found that the decomposition of organophosphorus compounds during and after recovery from their synthesis reaction mixtures can be prevented or minimized by adding an acid scavenger to the synthesis reaction mixture so as to provide at least 0.5% by weight of acid scavenger, based on the weight of the organophosphorus compound, before allowing the organophosphorus compound to crystallize.

DETAILED DESCRIPTION

The organophosphorus compounds which are stabilized in the practice of the invention may be any organophosphorus compounds containing acidic impurities—impurities which appear to be typically formed in the preparation of organophosphorus compounds. However, they are generally compounds corresponding to the formula:

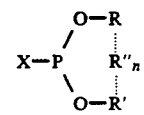

wherein R and R' are optionally-linked groups independently selected from alkyl, phenyl, and alkylated phenyl; R" is an alkylidene group containing 1-6 carbons; n is zero or one; and X represents hydrogen, chloro, fluoro, alkyl, alkoxy, hydroxy, phenoxy, or alkylated phenoxy.

Most commonly, the phosphites, phosphonites, and phosphonates described above are compounds in which any alkyl groups contain 1-20 carbons; and they include, e.g., trialkylphosphites, such as triethylphosphite, tridodecylphosphite, and trioctadecylphosphite; triarylphosphites, such as triphenylphosphite, tris(2,4-di-t-butylphenyl)phosphite, tris(dihexylphenyl)phosphite, tris(dinonylphenyl)phosphite, tris(nonylphenyl)phosphite, tris(octadecylphenyl)phosphite, bis(dioctadecylphenyl) octadecylphenyl phosphite, and bis(nonylphenyl) dinonylphenyl phosphite; alkyl aryl phosphites, such as dihexyl phenyl phosphite, diphenyl octadecyl phosphite, bis(nonylphenyl) dodecyl phosphite, didecyl tolyl phosphite, bis(2,6-di-t-butylphenyl)methyl phosphite, 2,2'-bis(4,6-di-t-butylphenyl)methyl phosphite, and 2,2'-ethylidenebis(4,6-di-t-butylphenyl)-methyl phosphite; diphosphaspiro compounds, such as the 3,9-bis(2,4-di-t-butylphenoxy)- and 3,9-bis(2,4,6-tri-t-butylphenoxy)-2,4,8,10-tetraoxy-3,9-diphosphaspiro[5.5]undecanes; hydrogen phosphites such as bis(2-methyl-6-t-butylphenyl)hydrogen phosphites 2,2'-bis(4,6-di-t-butylphenyl)hydrogen phosphites, and 2,2'-ethylidenebis(4,6-di-t-butylphenyl)hydrogen phosphite; and halophosphites, such as bis(2-methyl-6-t-butylphenyl)fluorophosphite, 2,2'-bis(4,6-di-t-butylphenyl)-fluorophosphite, 2,2'-methylenebis(4,6-di-t-butylphenyl)fluorophosphite,2,2'-ethylidenebis(4,6-di-t-butylphenyl)fluorophosphite,2,2'-isopropylidenebis(4,6-di-t-butylphenyl)fluorophosphite, and the corresponding chlorophosphites.

In a particularly preferred embodiment of the invention, the organophosphorus compound is a 2,2'-alkylidenebis(dialkylphenyl)fluorophosphite, a 2,2'-alkylidenebis(dialkylphenyl)alkyl phosphite, or a 2,2'-alkylidenebis(dialkylphenyl)hydrogen phosphite in which the alkylidene group contains 1-10 carbons and the alkyl groups are the same or different $C_1-C_6$ alkyl groups, most preferably in the 4- and 6-positions on the rings when ar-substituents.

The acid scavenger used to stabilize the organophosphorus compound may be any compound capable of scavenging the acidic residues present in the organophosphorus compound as prepared. However, it is preferably a metal carboxylate, oxide, or carbonate, such as a lithium, sodium, potassium, copper, zinc, cadmium, magnesium, calcium, barium, aluminum, or other metal carbonate, oxide, or salt of a carboxylic acid, e.g., a carboxylic acid containing 6-20 carbons, such as hexanoic, heptanoic, octanoic, decanoic, dodecanoic, tetradecanoic, hexadecanoic, stearic, or eicosanic acid. Among the particularly preferred stabilizers are calcium stearate, magnesium aluminum hydroxy carbonates, and the magnesium aluminum carbonate compositions known as talcites and hydrotalcites.

The amount of acid scavenger employed to stabilize the organophosphorus compound is at least 0.5%, preferably at least 2.5%, and most preferably at least 3%, based on the weight of the organophosphorus compound. Significant suppression of decomposition is observed at the lower levels of stabilizer, and the degree of suppression increases with increased loadings of stabilizer until close to complete prevention of decomposition is achieved at the 3% level. Although larger amounts of acid scavenger may be utilized if desired, the stabilizer loading is most commonly in the range of 0.5-10.0%, preferably 3-5%, based on the weight of the organophosphorus compound.

As already indicated, the organophosphorus compounds which are stabilized in the practice of the invention are compounds which have not yet been crystallized and are still present in their synthesis reaction mixtures, i.e., the reaction mixtures in which they were prepared. They are stabilized by adding the acid scavenger so as to achieve adequate mixing, and they are then recovered by conventional techniques, such as by (1) precipitating the product from the solvent in which it was prepared and then separating it by filtration or (2) exchanging the solvent used in the reaction for a different solvent, precipitating the product from the second solvent, and then isolating it by filtration.

The solvent exchange technique of recovering an organophosphorus compound is apt to be a preferred technique in the case of 2,2'-alkylidenebis(dialkylphenyl)fluorophosphites which have been prepared in a halohydrocarbon solvent, such as methylene chloride. In such a recovery process, (1) the crystallization solvent is typically added to a refluxing synthesis reaction mixture containing the organophosphorus compound product from which a portion of the solvent used in the reaction has been distilled, (2) heating is continued during the addition to remove the remainder of the solvent of the reaction, as well as some crystallization solvent, while the organophosphorus compound precipitates, (3) more crystallization solvent is added to the refluxing slurry, and (4) refluxing is continued for a suitable time (usually at least one hour) before the slurry is cooled to precipitate the solids and the precipitated solids are isolated by filtration.

When a crystallization solvent is employed in the recovery of an organophosphorus compound, it is quite understandably preferred to use a solvent which is relatively inexpensive, easy to handle, and low in toxicity. However, many of the crystallization solvents that have been preferred for those properties, e.g., water, acetonitrile, and alcohols, such as methanol, ethanol, 1-propanol, 2-propanol, 2-butanol, and t-butanol, have previously led to decomposition of the organophosphorus compound via hydrolysis and/or transesterification during the recovery processes utilizing them. An advantage of the present invention is that it minimizes or prevents the decomposition problems which normally accompany the use of such crystallization solvents and thereby makes their use more desirable.

The products obtained by the process of the invention are organophosphorus compounds containing the stabilizer used in their production. There is no need to separate the stabilizer from the organophosphorus compound, since the typical stabilizers are recognized to be harmless materials, and they do not prevent the organophosphorus compounds containing them from serving their normal functions, e.g., stabilization of organic polymers. In fact, it is preferable to retain the stabilizer in the organophosphorus compound to minimize or prevent decomposition during storage and/or during later use.

Stabilized organophosphorus compounds provided by the practice of the invention have the same utilities as the organophosphorus compounds provided by conventional techniques and can also be used in applications in which the known unstabilized compounds have sometimes been found to be ineffective because of decomposition problems now recognized to be caused by the presence of acidic residues in the organophosphorus compounds. For example, 2,2'-ethylidenebis(4,6-di-t-butylphenyl)fluorophosphite prepared by the process of the invention can be used to stabilize a polycarbonate against yellowing, as in U.S. Pat. No. 4,962,144 (Babillis et al.)—i.e., to incorporate 0.01-0.5% of the fluorophosphonite, based on the weight of the polycarbonate—without causing the polymer degradation that occurs when conventionally-prepared 2,2'-ethylidenebis(4,6-di-t-butylphenyl)fluorophosphite is used for that purpose and the resultant composition is exposed to moist steam for steam sterilization.

The following examples are given to illustrate the invention and are not intended as a limitation thereof. In these examples, codes are used to indicate certain compounds as follows:

| Compound | Code |
| --- | --- |
| 2,2'-ethylidenebis(4,6-di-t-butylphenyl)fluorophosphite | E-398 |
| 2,2'-ethylidenebis(4,6-di-t-butylphenyl)hydrogen phosphonate | AN-1126 |
| 2,2'-ethylidenebis(4,6-di-t-butylphenol) | AN-1008 |
| 2,4-di-t-butylphenol | AN-301 |
| 2,2'-ethylidenebis(4,6-di-t-butylphenyl)isopropyl phosphite | AN-1151 |
| 2,2'-ethylidenebis(4,6-di-t-butylphenyl)methyl phosphite | AN-1139 |

The first series of examples (Comparative Example A and Example 1), culminating in Table I, demonstrates how the addition of 2.5% by weight of talcite prior to crystallization increases the final yield and purity of E-398. The second series (Comparative Example B and Examples 2-7), the results of which are presented in Table II, shows that increasing the amount of talcite employed with E-398 in an alcoholic solvent decreases its decomposition into AN-1008, AN-1126, and AN-1151.

The third series of examples (Comparative Example C and Example 8), culminating in Table III, illustrates the stabilizing effect of calcium stearate on E-398 in refluxing alcoholic solvents.

The fourth series (Comparative Example D and Example 9), culminating in Table IV, is included to demonstrate the stabilizing effect of talcite on a different organophosphorus compound, i.e., AN-1139, in refluxing alcoholic solvent.

COMPARATIVE EXAMPLE A

Charge a suitable crystallization vessel with 350 g of a methylene chloride solution of an impure E-398 having the following analysis by gas chromatography (GC):

| Compound | Area % |
|---|---|
| E-398 | 92.0 |
| AN-1126 | 2.7 |
| AN-1008 | 1.7 |
| AN-301 | 0.7 |

Stir and heat the solution under nitrogen while collecting 150 g of methylene chloride in a Dean-Stark trap over a period of two hours. Then add 111 g of a 1% solution of water in 2-propanol while continuously collecting 121 g of methylene chloride and 2-propanol and allowing E-398 to precipitate. Add another 111 g of the 1% solution of water in 2-propanol while maintaing the slurry at reflux temperature. Then stir the slurry at reflux temperature for 40 hours, cool it to 30° C., and isolate the precipitated solids by filtration. After washing the collected solids with 100 mL of 2-propanol, air dry and weigh them, and subject them to GC analysis. Also concentrate the combined filtrate and wash on a rotary evaporator and weigh. The weights and analytical results are shown in Table I.

EXAMPLE 1

Repeat Comparative Example A except for adding an anhydrous talcite sold by Kyowa Chemical Industry as DHT-4C to the methylene chloride solution prior to the solvent exchange to provide 2.5% by weight of talcite, based on the weight of E-398. The weights and analytical results are shown in Table I.

TABLE I

| Example | A | 1 |
|---|---|---|
| Stabilizer/Amount | none | DHT-4C/2.5% |
| E-398 Yield (g) | 60 | 76.6[1] |
| E-398 Yield (%) | 70 | 87[1] |
| Residue Yield (g) | 25.5 | 11 |
| Product Analysis[2] | | |
| E-398 | 95.6 | 97.8 |
| AN-1008 | 2.1 | 0.7 |
| AN-1126 | 0.7 | 0.3 |

[1]Yield including retained DHT-4C
[2]GC Area %

COMPARATIVE EXAMPLE B

Combine 10 g of E-398 with 22 g of 2-propanol, 0.25 g of distilled water, 0.5 g of methylene chloride, 0.25 g of AN-1126, and 0.2 g of pyridine. Stir the resulting slurry at reflux temperature analyze it periodically by gas chromatography. The analytical results are shown in Table II.

EXAMPLES 2-7

Perform six experiments by repeating Comparative Example B except for also combining, respectively, 50 mg, 100 mg, 200 mg, 300 mg, 400 mg, and 500 mg of DHT-4C talcite with the E-398. The analytical results are shown in Table II.

TABLE II

| Ex. | Talcite (%) | Time (hrs.) | E-398 | AN-1008 | AN-1126 | AN-1151 |
|---|---|---|---|---|---|---|
| B | 0 | 1 | 95.4 | 1.1 | 2.1 | nd[1] |
|   | 0 | 5 | 95.9 | 2.3 | 1.0 | 0.2 |
|   | 0 | 22 | 83.5 | 13.3 | 0.8 | 1.2 |
|   | 0 | 29 | 70.3 | 23.8 | 1.6 | 1.2 |
|   | 0 | 46 | 40.0 | 52.2 | 5.3 | 1.8 |
|   | 0 | 53 | 18.2 | 71.6 | 6.1 | 1.7 |
| 2 | 0.5 | 1 | 96.2 | 1.4 | 1.5 | nd[1] |
|   | 0.5 | 5 | 95.8 | 2.2 | 0.9 | 0.2 |
|   | 0.5 | 22 | 91.3 | 5.7 | 0.5 | 1.2 |
|   | 0.5 | 29 | 86.5 | 10.5 | 0.6 | 1.5 |
|   | 0.5 | 46 | 61.0 | 33.9 | 2.6 | 1.9 |
|   | 0.5 | 53 | 42.6 | 48.9 | 4.9 | 2.9 |
| 3 | 1.0 | 1 | 96.3 | 1.5 | 1.3 | nd[1] |
|   | 1.0 | 5 | 96.2 | 2.0 | 0.9 | 0.2 |
|   | 1.0 | 22 | 92.0 | 4.1 | 0.6 | 1.4 |
|   | 1.0 | 29 | 89.9 | 6.7 | 0.6 | 1.6 |
|   | 1.0 | 46 | 70.3 | 25.2 | 1.1 | 1.9 |
|   | 1.0 | 53 | 60.3 | 37.5 | 2.2 | 2.2 |
| 4 | 2.0 | 1 | 96.7 | 1.2 | 1.8 | nd[1] |
|   | 2.0 | 5 | 96.3 | 1.8 | 1.1 | nd[1] |
|   | 2.0 | 22 | 94.5 | 3.3 | 0.8 | 1.0 |
|   | 2.0 | 29 | 92.9 | 4.1 | 1.0 | 1.7 |
|   | 2.0 | 46 | 87.7 | 8.0 | 1.3 | 2.6 |
|   | 2.0 | 53 | 83.0 | 13.1 | 1.0 | 2.4 |
| 5 | 3.0 | 1 | 96.8 | 1.2 | 1.7 | nd[1] |
|   | 3.0 | 5 | 96.6 | 1.7 | 1.2 | nd[1] |
|   | 3.0 | 22 | 94.5 | 3.4 | 0.8 | 0.5 |
|   | 3.0 | 29 | 95.2 | 3.0 | 0.6 | 0.8 |
|   | 3.0 | 46 | 92.5 | 4.1 | 0.5 | 1.8 |
|   | 3.0 | 53 | 92.7 | 4.2 | 0.5 | 2.0 |
| 6 | 4.0 | 1 | 96.6 | 1.2 | 1.9 | nd[1] |
|   | 4.0 | 5 | 96.8 | 1.9 | 1.0 | nd[1] |
|   | 4.0 | 22 | 96.0 | 2.9 | 0.5 | 0.4 |
|   | 4.0 | 46 | 92.5 | 4.8 | 0.6 | 1.8 |
|   | 4.0 | 53 | 92.7 | 4.6 | 0.6 | 1.9 |
| 7 | 5.0 | 1 | 96.6 | 1.1 | 1.9 | nd[1] |
|   | 5.0 | 5 | 96.9 | 1.8 | 1.0 | nd[1] |
|   | 5.0 | 22 | 95.9 | 3.0 | 0.5 | 0.3 |
|   | 5.0 | 46 | 94.6 | 3.7 | 0.4 | 0.9 |
|   | 5.0 | 53 | 93.3 | 4.8 | 0.4 | 1.3 |

[1]nd - none detected

COMPARATIVE EXAMPLE C

Repeat Comparative Example B except for including no pyridine in the slurry. The analytical results are shown in Table III.

EXAMPLE 8

Repeat Comparative Example C except for also combining 300 mg of calcium stearate with the E-398. The analytical results are shown in Table III.

TABLE III

| Ex. | CaSt (%) | Time (hrs.) | E-398 | AN-1008 | AN-1126 | AN-1151 |
|---|---|---|---|---|---|---|
| C | 0 | 1 | 96.6 | 1.3 | 1.7 | nd[1] |
|   | 0 | 2 | 96.7 | 1.3 | 1.8 | nd[1] |
|   | 0 | 3 | 96.7 | 1.3 | 1.7 | 0.1 |
|   | 0 | 4 | 95.9 | 1.5 | 1.6 | 0.2 |
|   | 0 | 5 | 96.3 | 1.7 | 1.6 | 0.3 |
|   | 0 | 22 | 82.9 | 9.8 | 6.1 | 0.3 |
|   | 0 | 29 | 26.0 | 46.1 | 25.9 | 1.3 |
| 8 | 3.0 | 1 | 97.7 | 1.3 | 1.1 | nd[1] |
|   | 3.0 | 5 | 96.2 | 1.9 | 0.6 | nd[1] |
|   | 3.0 | 22 | 97.4 | 2.0 | 0.4 | 0.1 |
|   | 3.0 | 29 | 96.4 | 2.5 | 0.5 | 0.2 |
|   | 3.0 | 46 | 96.9 | 2.4 | 0.4 | 0.3 |

TABLE III-continued

| Ex. | CaSt (%) | Time (hrs.) | GC Area % Analysis | | |
|---|---|---|---|---|---|
| | | | E-398 | Decomposition Products | |
| | | | | AN-1008 | AN-1126 | AN-1151 |
| | 3.0 | 53 | 96.8 | 2.3 | 0.3 | 0.3 |

[1]nd - none detected

COMPARATIVE EXAMPLE D

Combine 2 g of AN-1139 with 8 g of 2-propanol, and 0.12 g of distilled water. Stir the resulting slurry at reflux temperature and analyze it periodically by gas chromatography. The analytical results are shown in Table IV.

EXAMPLE 9

Repeat Comparative Example D except for also combining 100 mg of DHT-4C talcite with the AN-1139. The analytical results are shown in Table IV.

TABLE IV

| Ex. | Talcite (%) | Time (hrs.) | GC Area % Analysis | | |
|---|---|---|---|---|---|
| | | | AN-1139 | Decomposition Products | |
| | | | | AN-1126 | AN-1008 |
| D | 0 | 1 | 97.4 | 0.4 | 1.0 |
| | 0 | 3 | 96.9 | 1.5 | 0.8 |
| | 0 | 6 | 40.9 | 41.9 | 11.5 |
| | 0 | 22 | nd[1] | 40.9 | 55.8 |
| 9 | 5 | 1 | 98.8 | 0.3 | 0.4 |
| | 5 | 3 | 98.5 | 0.3 | 0.6 |
| | 5 | 6 | 95.1 | 0.3 | 1.7 |
| | 5 | 22 | 97.4 | 0.3 | 1.3 |

[1]nd - none detected

What is claimed is:

1. In a process for recovering an organophosphorus compound from its synthesis reaction mixture, the improvement which comprises minimizing or preventing its decomposition by adding to the synthesis reaction mixture at least 0.5% by weight of an acid scavenger, based on the weight of the organophosphorus compound, before allowing the organophosphorus compound to crystallize.

2. The process of claim 1 wherein the organophosphorus compound is a compound corresponding to the formula:

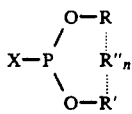

in which R and R' are optionally-linked groups independently selected from alkyl, phenyl, and alkylated phenyl; R" is an alkylidene group containing 1-6 carbons; n is zero or one; and X represents hydrogen, chloro, fluoro, alkyl, alkoxy, hydroxy, phenoxy, or alkylated phenoxy.

3. The process of claim 2 wherein the organophosphorus compound is a 2,2'-alkylidenebis(dialkylphenyl)-fluorophosphite in which the alkylidene group contains 1-10 carbons and the alkyl groups are the same or different $C_1$-$C_6$ alkyl groups.

4. The process of claim 3 wherein the organophosphorus compound is 2,2'-ethylidenebis(4,6-di-t-butyl-phenyl)fluorophosphite.

5. The process of claim 2 wherein the organophosphorus compound is a 2,2'-alkylidenebis(dialkylpheny-l)alkyl phosphite in which the alkylidene group contains 1-10 carbons and the alkyl groups are the same or different $C_1$-$C_6$ alkyl groups.

6. The process of claim 5 wherein the organophosphorus compound is 2,2'-ethylidenebis(4,6-di-t-butyl-phenyl)methyl phosphite.

7. The process of claim 2 wherein the organophosphorus compound is a 2,2'-alkylidenebis(dialkylphenyl)-hydrogen phosphite in which the alkylidene group contains 1-10 carbons and the alkyl groups are the same or different $C_1$-$C_6$ alkyl groups.

8. The process of claim 7 wherein the organophosphorus compound is 2,2'-ethylidenebis(4,6-di-t-butyl-phenyl)hydrogen phosphite.

9. The process of claim 1 wherein the acid scavenger is a metal carboxylate, oxide, or carbonate.

10. The process of claim 9 wherein the acid scavenger is a metal carbonate.

11. The process of claim 10 wherein the metal carbonate is an anhydrous talcite.

12. The process of claim 10 wherein the metal carbonate is a hydrotalcite.

13. The process of claim 9 wherein the acid scavenger is a metal carboxylate.

14. The process of claim 13 wherein the metal carboxylate is calcium stearate.

15. The process of claim 1 wherein the amount of acid scavenger added to the synthesis reaction mixture is 0.5-10.0%, based on the weight of the organophosphorus compound.

16. The process of claim 15 wherein the amount of acid scavenger is 3-5%, based on the weight of the organophosphorus compound.

17. In a process for recovering from its synthesis reaction mixture a 2,2'-alkylidenebis(dialkylphenyl)-fluorophosphite which has been prepared in a halohydrocarbon solvent by (1) refluxing the reaction mixture to remove a portion of the halohydrocarbon solvent, (2) adding a crystallization solvent selected from heptane, water, acetonitrile, and alcohols to the refluxing mixture while continuing to remove halohydrocarbon solvent to replace it with the crystallization solvent and permit crystallization of the 2,2'-alkylidenebis(dialkyl-phenyl)fluorophosphite, (3) adding supplemental crystallization solvent, (4) after refluxing the resulting slurry, cooling it to precipitate the solids, and (5) isolating the precipitated solids by filtration, the improvement which comprises minimizing or preventing decomposition of the 2,2'-alkylidenebis(dialkylphenyl)-fluorophosphonite by adding to the synthesis reaction mixture at least 0.5%, based on the weight of the 2,2'-alkylidenebis(dialkylphenyl)fluorophosphite, an acid scavenger selected from metal carboxylates, oxides, and carbonates prior to exchanging the crystallization solvent for the halohydrocarbon solvent.

18. The process of claim 17 wherein the 2,2'-alkylidenebis(dialkylphenyl)fluorophosphite is 2,2'-ethylidenebis(4,6-di-t-butylphenyl)fluorophosphite, the acid scavenger is a talcite, and the amount of acid scavenger is 3-5%, based on the weight of the fluorophosphite.

19. The process of claim 17 wherein the 2,2'-alkylidenebis(dialkylphenyl)fluorophosphite is 2,2'-ethylidenebis(4,6-di-t-butylphenyl)fluorophosphite, the acid scavenger is calcium stearate, and the amount of acid scavenger is 3-5%, based on the weight of the fluorophosphite.

* * * * *